US012622677B2

(12) United States Patent
Zhou et al.

(10) Patent No.: US 12,622,677 B2
(45) Date of Patent: May 12, 2026

(54) MULTI-MODE ROLLING-ENCODED ULTRASOUND

(71) Applicant: FUJIFILM SonoSite, Inc., Bothell, WA (US)

(72) Inventors: Yong Zhou, Woodinville, WA (US); Jean Tsou, Seattle, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 174 days.

(21) Appl. No.: 18/593,339

(22) Filed: Mar. 1, 2024

(65) Prior Publication Data

US 2025/0275753 A1 Sep. 4, 2025

(51) Int. Cl.
*A61B 8/00* (2006.01)
(52) U.S. Cl.
CPC ............ *A61B 8/5207* (2013.01); *A61B 8/486* (2013.01); *A61B 8/488* (2013.01); *A61B 8/5269* (2013.01)

(58) Field of Classification Search
CPC ..... A61B 8/5207; A61B 8/5269; A61B 8/486; A61B 8/488
See application file for complete search history.

(56) References Cited

U.S. PATENT DOCUMENTS

2018/0206820 A1 *  7/2018  Anand ................ G01S 7/52085
2019/0167234 A1 *  6/2019  Wegner ................. A61B 8/463

* cited by examiner

*Primary Examiner* — Chao Sheng
(74) *Attorney, Agent, or Firm* — Colby Nipper PLLC

(57) ABSTRACT

Systems and methods for a multi-mode rolling-encoded ultrasound are described. These systems and methods include an ultrasound device that provides an encoded ultrasound signal, which includes one or more multi-mode waveforms that contain multiple mode types, multiple variants from a single mode type, or a mixture of such. The encoded ultrasound signals are used to image or otherwise gather information from a target during an ultrasound scan, such as a portion of a patient anatomy. The reflected encoded signals are received and decoded, resulting in an increased resolution and frame rate. This allows for more-efficient operation and resource utilization.

20 Claims, 10 Drawing Sheets

300

100

200

300

400

600

700

1000

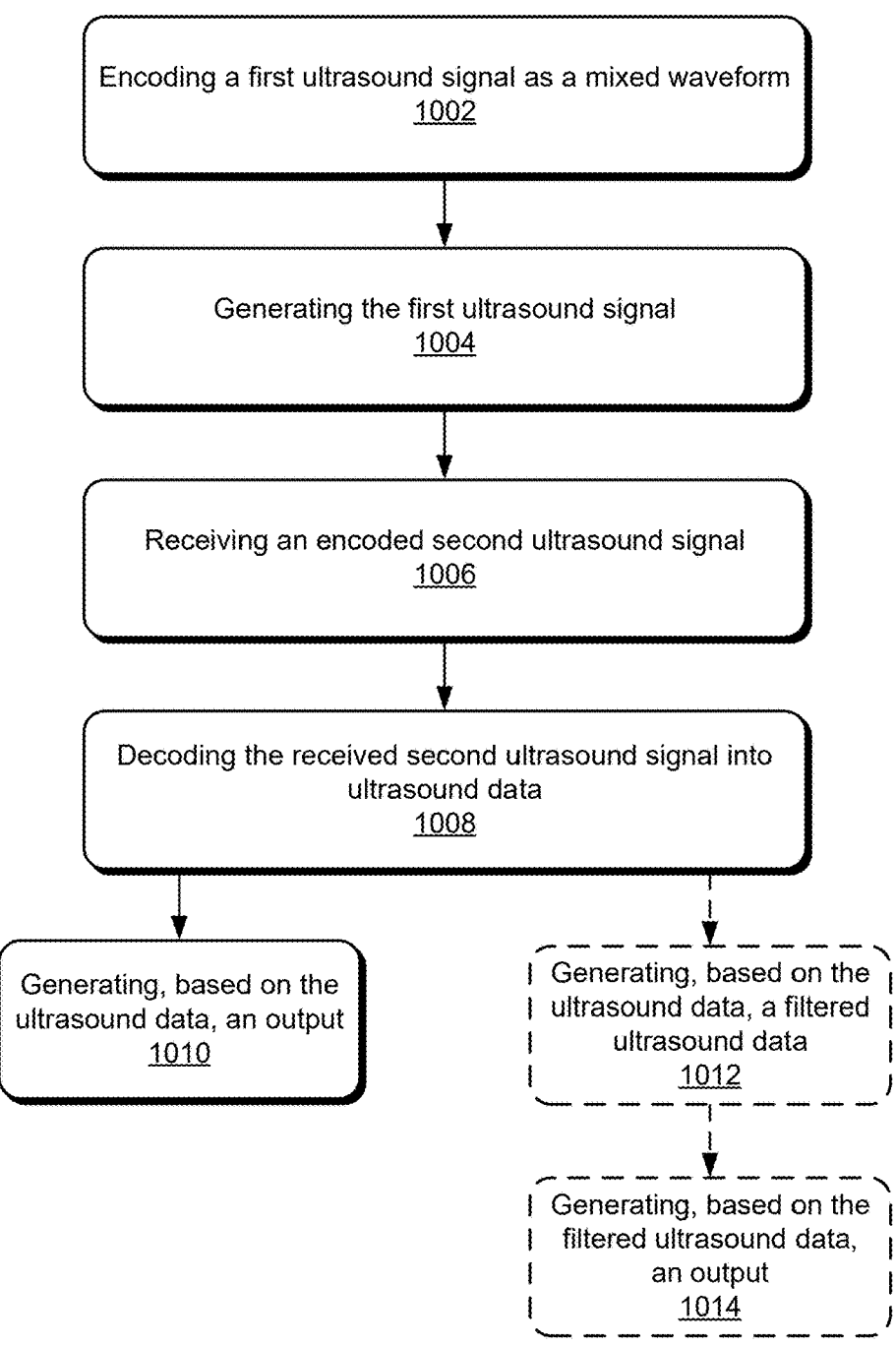

Encoding a first ultrasound signal as a mixed waveform
1002

Generating the first ultrasound signal
1004

Receiving an encoded second ultrasound signal
1006

Decoding the received second ultrasound signal into ultrasound data
1008

Generating, based on the ultrasound data, an output
1010

Generating, based on the ultrasound data, a filtered ultrasound data
1012

Generating, based on the filtered ultrasound data, an output
1014

*Fig. 10*

MULTI-MODE ROLLING-ENCODED ULTRASOUND

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and can provide immediate imaging results, ultrasound systems are used ubiquitously. In ultrasound imaging, less artifacts, better resolution and penetration, and faster frame rate are always desired. However, in real applications, because of the limitations due to physics, safety, etc., often there is a compromise scenario involving unwanted artifacts, unideal resolution, inadequate penetration, or a low frame rate, to name a few.

In certain ultrasound modes (e.g., triplex), there are obvious band artifacts in the pulsed-wave (PW) Doppler spectrum due to data discontinuity. In some applications, the resolution, penetration, frame rate, or any number of other factors may not be sufficient due to the patient type. Even with parameters at their current technological limit, it is always preferable to have these properties (e.g., frame rate, resolution, etc.) enhanced for more accurate information and better diagnosis results. Current methods are aimed at solving the artifact issue and/or improving the image properties (e.g., resolution, penetration, frame rate, etc.), but they all have drawbacks and trade-offs. For example, to address the artifact issue in PW spectrum, extrapolation is used to estimate the missing data. However, it is still an approximation, and cannot remove the artifacts completely. In another example, signal frequency can be lowered to provide better penetration, but this results in a loss of resolution.

A robust solution is needed to realize higher resolution and frame rate without the sacrifices and trade-offs endemic to current methodologies.

SUMMARY

Devices and methods for a multi-mode rolling-encoded ultrasound are described. These systems and methods include an ultrasound device that provides an encoded ultrasound signal, which includes one or more multi-mode waveforms that contain multiple mode types, multiple variants from a single mode type, or a mixture of such. The encoded ultrasound signals are used to image or otherwise gather information from a target during an ultrasound scan, such as a portion of a patient anatomy. The reflected encoded signals are received and decoded, resulting in an increased resolution and frame rate. This allows for more-efficient operation and resource utilization compared to conventional ultrasound systems.

In some implementations, an ultrasound device is disclosed. The ultrasound device includes an ultrasound scanner configured to generate an ultrasound signal, where the ultrasound signal includes a plurality of ultrasound signal modes and is configured for transmission by the ultrasound scanner at a subject. The ultrasound device further includes, in aspects, one or more processors and a memory. The memory stores instructions that, when executed by the one or more processors, cause the one or more processors to encode the ultrasound signal as a mixed waveform. The encoding is based on the plurality of ultrasound signal modes. According to some examples, the plurality of ultrasound signal modes includes two or more of an amplitude mode ("A-mode"), a brightness mode ("B-mode"), a motion mode ("M-mode"), a Doppler-based mode, etc., or different variants of these modes. In aspects, the instructions further cause the one or more processors to transmit the encoded ultrasound signal at the subject. The transmission, in aspects, is performed by the ultrasound scanner. In some examples, encoding the ultrasound signal includes combining the plurality of ultrasound signal modes based on one or more of a polarity, a time of transmission, or a location of transmission. In aspects, the plurality of ultrasound signal modes is combined using an orthogonal matrix operator. In some examples, at least one of the plurality of ultrasound signal modes is a non-image-based signal mode.

In some implementations, an ultrasound device is disclosed. The ultrasound device includes an ultrasound scanner, and the ultrasound scanner is configured to receive an encoded ultrasound signal. The encoded ultrasound signal includes reflections of a plurality of ultrasound signal modes from a subject. The ultrasound device also includes one or more processors and a memory, where the memory stores instructions that, when executed by the one or more processors, cause the one or more processors to decode the received encoded ultrasound signal into ultrasound data. The ultrasound data includes the plurality of ultrasound signal modes. According to some examples, the plurality of ultrasound signal modes includes two or more of an A-mode, a B-mode, an M-mode, a Doppler-based mode, etc., or different variants of these modes. In aspects, the decoding of the received encoded ultrasound signal into the ultrasound data is based on one or more of a polarity, a time of transmission, or a location of transmission for the encoded ultrasound signal. According to some examples, the instructions further cause the one or more processors to produce an output based on the ultrasound data. The output can be an image of an anatomy of the subject, a determination of a speed of sound, a determination of a background noise, or a detection of one or more artifacts. According to some examples, the instructions further cause the one or more processors to generate a filtered ultrasound data based on the ultrasound data. In aspects, the decoding of the received encoded ultrasound signal into the ultrasound data includes processing the received encoded ultrasound signal using an orthogonal matrix operator, and the orthogonal matrix operator can be based on a Fourier transformation.

In some implementations, an ultrasound device is disclosed. The ultrasound device includes an ultrasound scanner, and the ultrasound scanner is configured to generate a first ultrasound signal. The first ultrasound signal includes a plurality of ultrasound signal modes. The first ultrasound signal is configured for transmission by the ultrasound scanner at a subject. The ultrasound scanner is further configured to receive an encoded ultrasound signal, and the encoded ultrasound signal includes reflections of the plurality of ultrasound signal modes from the subject. The ultrasound device further includes one or more processors and a memory. The memory stores instructions that, when executed by the one or more processors, cause the one or more processors to encode the first ultrasound signal as a mixed waveform. The encoding of the first ultrasound signal is based on the plurality of ultrasound signal modes. The one or more processors are further caused to, based on the received encoded ultrasound signal, decode the received encoded ultrasound signal into second ultrasound data. The second ultrasound data includes the plurality of ultrasound signal modes. In aspects, the plurality of ultrasound signal modes are two or more of an A-mode, a B-mode, an M-mode, a Doppler-based mode, or different variants of these modes. According to some examples, the encoding of the first ultrasound signal and the decoding of the received encoded ultrasound signal includes processing the plurality of ultrasound signal modes and the received encoded ultrasound signal, respectively, using an orthogonal matrix operator. In aspects, the instructions further cause the one or more processors to produce a filtered ultrasound data. The filtered ultrasound data is based on the second ultrasound signal, and the one or more processors are further caused to produce, based on the filtered ultrasound data, an output. In some examples, the output is an image of an anatomy of the subject, a determination of a speed of sound, a determination of a background noise, or a detection of one or more artifacts. According to some examples, the instructions further cause the one or more processors to transmit, by the ultrasound scanner, the first encoded ultrasound signal at the subject.

In some implementations, a method for encoding and decoding a multi-mode rolling-encoded ultrasound signals is disclosed. The method includes encoding, by one or more processors, a first ultrasound signal as a mixed waveform, the first ultrasound signal. The encoding is based on a plurality of ultrasound signal modes. The encoded first ultrasound signal includes the plurality of ultrasound signal modes and is configured for transmission by the ultrasound scanner at a subject. The method, in aspects, further includes generating, by an ultrasound scanner, the first ultrasound signal. In some examples, the method further includes receiving, by the ultrasound scanner and from the subject, an encoded second ultrasound signal. The encoded second ultrasound signal includes reflections of the plurality of ultrasound signal modes. The method, in aspects, further includes decoding the received encoded second ultrasound signal into ultrasound data. The decoding is based on the received encoded second ultrasound signal, and the ultrasound data includes the plurality of ultrasound signal modes.

Other devices and methods to provide a multi-mode rolling-encoded ultrasound are also described. These other devices and methods, in addition to those already disclosed, can be combined to generate additional devices and methods, which, though not explicitly disclosed herein, still are the same in concept as the devices and methods described explicitly herein. The devices and methods explicitly outlined herein are meant to be illustrative and not limiting.

BRIEF DESCRIPTION OF THE DRAWINGS

The appended drawings illustrate examples and are, therefore, exemplary embodiments and not considered to be limiting in scope.

FIG. 10 outlines a method for a multi-mode rolling-encoded ultrasound.

DETAILED DESCRIPTION

Conventional ultrasound systems can generate noisy ultrasound images that can result in unideal outcomes and/or failures, such as misclassifications of blood vessels, improper anatomy segmentations, etc. Hence, a patient may not receive the best care possible. Accordingly, systems, devices, and methods are disclosed herein that increase ultrasound resolution without sacrificing frame rate, resulting in a clearer and more accurate ultrasound process compared to conventional ultrasound systems.

Moreover, an increase in resolution and/or frame rate enables a reduction in undesirable artifacts. Artifacts in ultrasound imagery or processing can present difficulties in identification of anatomy, false positives for present phenomena (e.g., portions of an anatomy, presence of tumors, etc.), or any number of other, unwanted or unideal outcomes from an ultrasound examination. By reducing the number and/or severity of artifacts, a multi-mode rolling-encoded ultrasound enhances the efficacy of an ultrasound examination and related diagnoses.

Figure 1:
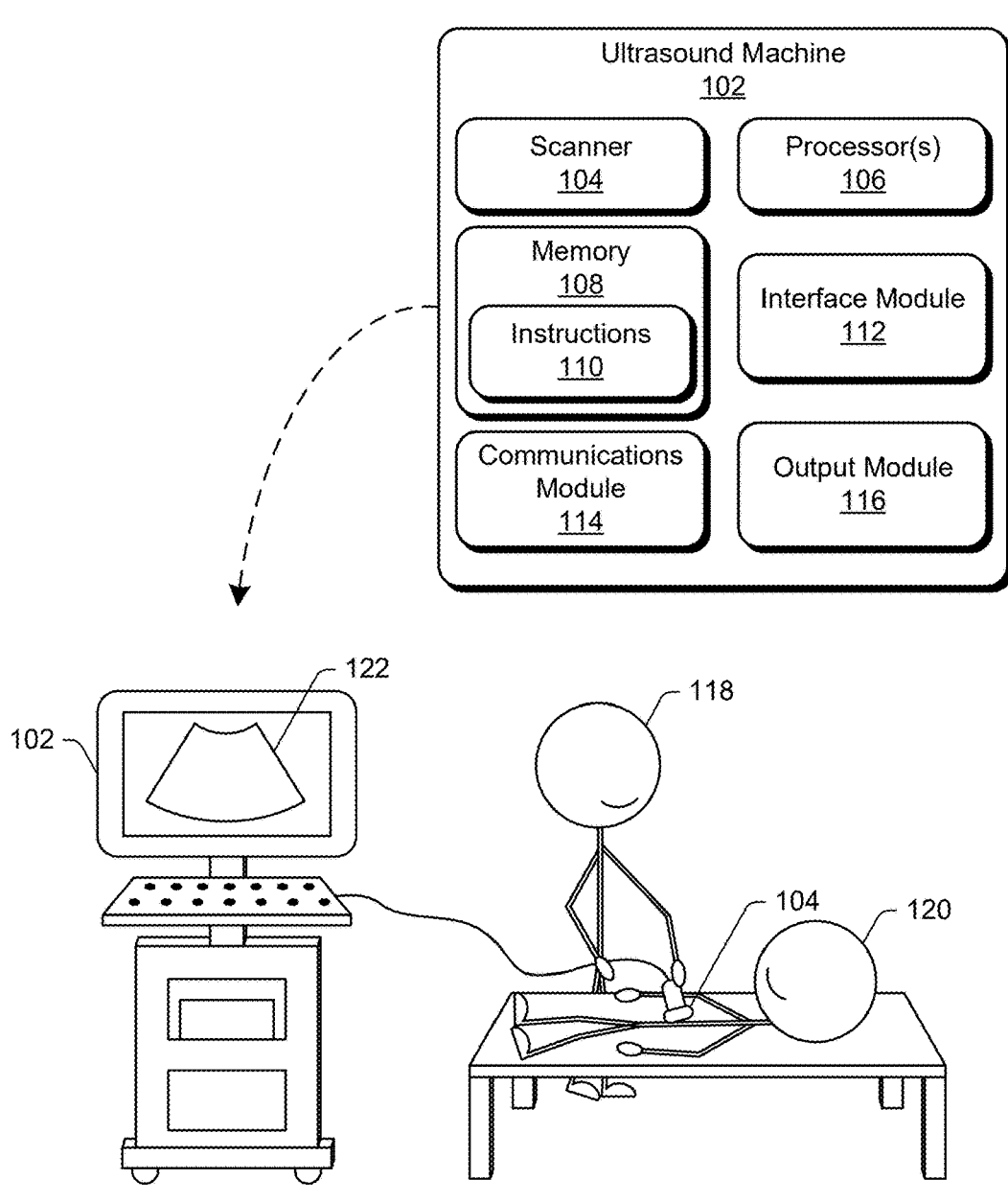
FIG. 1 illustrates an example environment for a multi-mode rolling-encoded ultrasound device in accordance with one or more implementations.

In some embodiments, the multi-mode rolling-encoded ultrasound system provides not just ultrasound images but also information related to the examination or examination conditions, such as a speed of sound in the examined medium, a background noise level, a characteristic of the background noise, or other parameters that can be useful in evaluating signals received from an ultrasound examination.
Example System FIG. 1 illustrates an example environment 100 for an ultrasound machine 102, in accordance with one or more implementations. Generally, the ultrasound machine 102 includes various components, some of which include a scanner 104, one or more processors 106, a memory 108 storing instructions 110, an interface module 112, a communications module 114, and an output module 116.

A user 118 (e.g., nurse, ultrasound technician, clinician, operator, sonographer, etc.) directs the scanner 104 toward a patient 120 to non-invasively scan internal bodily structures (e.g., anatomies, organs, tissues, etc.) of the patient 120 for testing, diagnostic, or therapeutic reasons. In some implementations, the scanner 104 includes an ultrasound transducer array and electronics communicatively coupled to the ultrasound transducer array to transmit ultrasound signals to the patient's anatomy and receive ultrasound signals reflected from the patient's anatomy (e.g., echoes). In some implementations, the scanner 104 is an ultrasound scanner, which can also be referred to as an ultrasound probe or transducer. In aspects, the scanner 104 is configured to produce and receive encoded ultrasound signals, the encoded ultrasound signals comprising two or more ultrasound mode types, two or more variants of a single mode type, or a combination of mode types and mode type variants. For brevity, the present disclosure can refer to all of these as simply "mode types" or "modes."

The output module 116 can be, in some examples, a display such as a display 122. The output module 116 is coupled to the one or more processors 106, which process the reflected ultrasound signals to generate ultrasound data. The output module 116 is, according to some examples, configured to generate and display an ultrasound image of the anatomy based on the ultrasound data generated by the one or more processors 106 from the reflected ultrasound signals detected by the scanner 104. In aspects, the ultrasound data includes the ultrasound image or data representing the ultrasound image. In aspects, the output module 116 is configured to generate a non-image output based on the ultrasound data, such as a speed of sound in the medium of the patient 120 anatomy, a background noise, or other non-image information.

Figure 2:
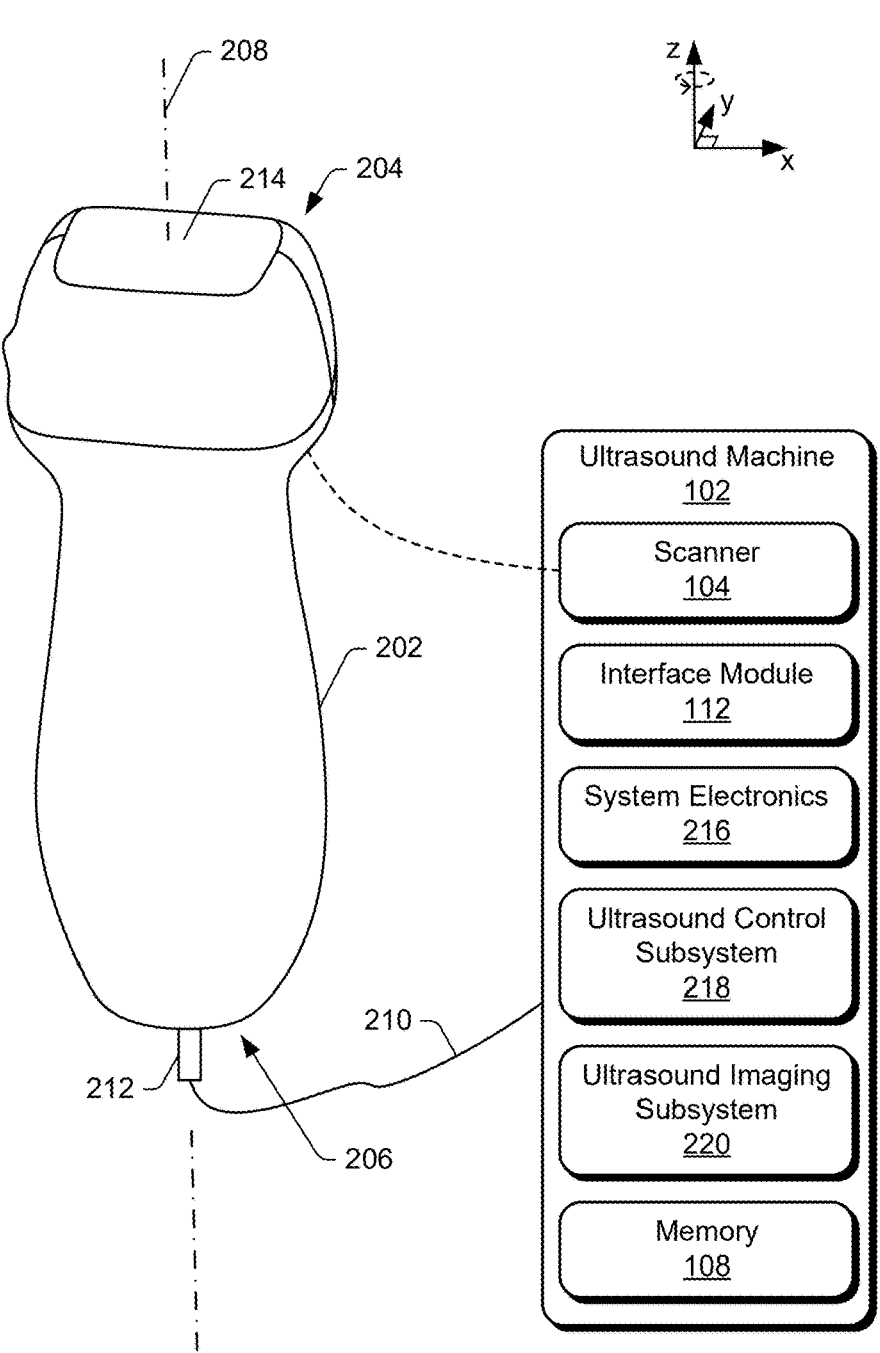
FIG. 2 illustrates an example implementation of the ultrasound system from FIG. 1.

FIG. 2 illustrates an example implementation 200 of the ultrasound machine 102 from FIG. 1. The scanner 104 (e.g., ultrasound scanner) includes an enclosure 202 extending between a distal end portion 204 and a proximal end portion 206. The enclosure 202 includes a central axis 208 (e.g., longitudinal axis) that intersects the distal end portion 204 and the proximal end portion 206. The central axis 208 corresponds to an axial direction of the scanner 104. In an example, the scanner 104 is electrically coupled to an ultrasound imaging system (e.g., the ultrasound machine 102) via a cable 210 that is attached to the proximal end portion 206 of the scanner 104 by a strain-relief element 212. In some implementations, the scanner 104 is wirelessly coupled to the ultrasound imaging system and communicates with the ultrasound imaging system via one or more wireless transmitters, receivers, or transceivers over a wireless connection or network (e.g., Bluetooth™, Wi-Fi™, etc.).

A transducer assembly 214 having one or more transducer elements is electrically coupled to system electronics 216 in the ultrasound machine 102. In operation, the transducer assembly 214 transmits ultrasound energy from the one or more transducer elements toward a subject and receives ultrasound echoes from the subject. The ultrasound echoes are converted into electrical signals by the transducer element(s) and electrically transmitted to the system electronics 216 in the ultrasound machine 102 for processing and generation of one or more ultrasound images.

Capturing ultrasound data from a subject using a transducer assembly (e.g., the transducer assembly 214) generally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 megahertz (MHz)) and/or high-frequency ultrasound (e.g., greater than or equal to 15 MHZ). A particular frequency range to use can readily be determined based on various factors (e.g., depth of imaging, desired resolution, etc.).

In some implementations, the system electronics 216 include one or more processors (e.g., the processor(s) 106 from FIG. 1), integrated circuits, application-specific integrated circuits (ASICs), Field Programmable Gate Arrays (FPGAs), Graphics Processing Units (GPUs) and power sources to support functioning of the ultrasound machine 102. In some implementations, the ultrasound machine 102 also includes an ultrasound control subsystem 218 having one or more processors. At least one processor, FPGA, ASIC, GPU, etc. causes electrical signals to be transmitted to the transducer(s) of the scanner 104 to both emit sound waves and also receive electrical pulses from the scanner 104 that were created from the returning echoes. One or more processors, FPGAs, ASICs, GPUs, etc. process the raw data associated with the received electrical pulses and form an image that is sent to an ultrasound imaging subsystem 220, which causes the image to be displayed (e.g., via the output module 116). In aspects, the output module 116 displays ultrasound images from the ultrasound data processed by the processor(s) of the ultrasound control subsystem 218.

In some implementations, the ultrasound machine 102 also includes one or more user input devices (e.g., a keyboard, a cursor control device, a microphone, a camera, etc.) that input data and enable taking measurements, such as from a display from output module 116 of the ultrasound machine 102. The ultrasound machine 102 can also include a disk storage device (e.g., computer-readable storage media such as read-only memory (ROM), a Flash memory, a dynamic random-access memory (DRAM), a NOR memory, a static random-access memory (SRAM), a NAND memory, etc.) for storing the acquired ultrasound data. In aspects, the disk storage device includes the memory 108, which is local to the ultrasound machine 102. Alternatively, the memory 108 used for storing the acquisition data can be remote, such as on a remote server communicatively connected to the ultrasound machine 102. In addition, the ultrasound machine 102 can include a printer that prints the image from the displayed data. To avoid obscuring the techniques described herein, some elements, such user input devices, disk storage device, and printer, are not shown in FIG. 2.

Example Encoding and Decoding

Figure 3:
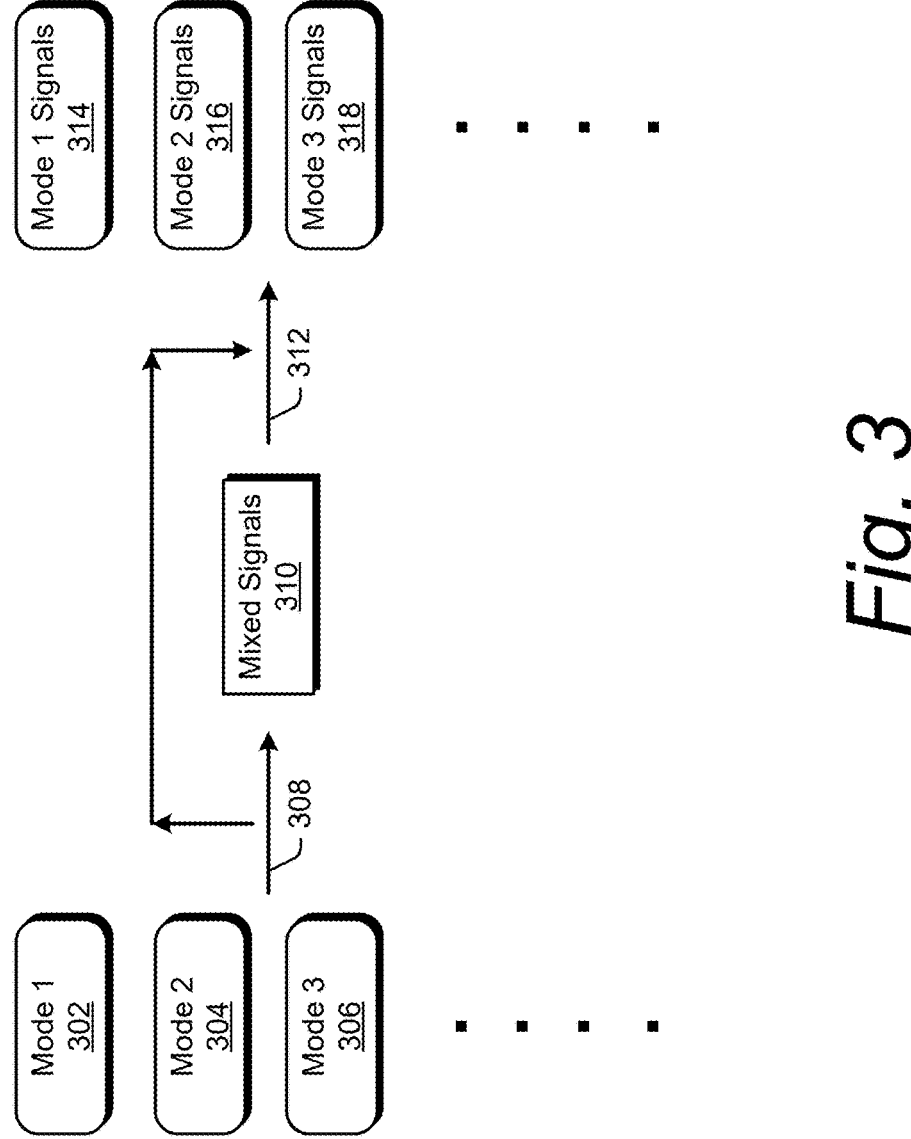
FIG. 3 illustrates a block diagram showing the concept of encoding and decoding signals in a multi-mode rolling-encoded ultrasound.

FIG. 3 illustrates a block diagram 300 showing the concept of encoding and decoding signals in a multi-mode rolling-encoded ultrasound. Diagram 300 illustrates a multi-mode rolling-encoded ultrasound method. There are, in aspects, outgoing modes Mode 1 302, Mode 2 304, Mode 3 306, etc. The Modes 1, 2, 3, etc. (302, 304, 306, etc.) are, according to some examples, transmitted 308 as mixed signals 310. In aspects, the transmission 308 includes an encoding of the Modes 302, 304, and 306 into the mixed signal 310 form. In aspects, the mixed signals 310 include waveforms with different polarities (positive or negative) to encode with different patterns.

In some examples, the encoding of the mixed signals 310 can be performed using an orthogonal operator. For example, each waveform can be first correlated with different, specific mode types (e.g., B-mode, M-mode, A-mode, a Doppler-based mode such as color, PW, Tissue Doppler Imaging ("TDI"), Continuous Wave Doppler ("CW"), etc.) or with the same mode with different delays or apertures. For example, the mixed signals 310 can be encoded with both B-mode and PW mode types. In another example, B-mode imaging with different beam angles or different focal depths or different focal-spot sizes can also be used for encoding the mixed signals 310. In aspects, the same method can be extended to all the other modes, including M-mode, color, PW, TDI, CW, etc. In some examples, any of the combinations of the above modes and/or different angles, different focal depths, or different focal-spot sizes can be encoded. In general, any combinations in terms of different delays, weights, or waveforms in the transmit events can also, in aspects, be encoded into the mixed signals 310.

In aspects, there are several different ways to perform the encoding itself (e.g., Hadamard encoding, Fourier encoding, etc.). In some examples, any orthogonal basis can be used as the encoding mechanism. The following discussion uses Hadamard matrix encoding and decoding as exemplary, but it should be understood that similar formulations with equivalent results can be realized using other encoding and decoding schemes (e.g., Fourier encoding, other orthogonal matrix formulations, non-orthogonal or non-matrix formulations, etc.). For example, to encode two mode types or two forms of the same mode type, a bipolar Hadamard matrix can be employed of a size two by two:

$$\begin{bmatrix} 1 & 1 \\ 1 & -1 \end{bmatrix} \qquad \text{Matrix 1}$$

Alternatively, a unipolar Hadamard matrix can be employed of a size two by two:

$$\begin{bmatrix} 1 & 1 \\ 1 & 0 \end{bmatrix} \qquad \text{Matrix 2}$$

The negative sign in the bipolar Hadamard matrix of Matrix 1 represents the polarity of the transmit waveform. Note that the negative forms of the Hadamard matrix are mathematically identical in implementation to the positive matrices discussed above. For example, the negative forms of the Hadamard matrix are as follows:

$$\begin{bmatrix} -1 & -1 \\ -1 & 1 \end{bmatrix} \text{ or } \begin{bmatrix} -1 & -1 \\ -1 & 0 \end{bmatrix} \qquad \text{Matrix 3 \& 4}$$

For simplicity, only the bipolar form of the orthogonal basis for the encode and decode process is described below, but this should not be seen as limiting. Any of the other forms previously disclosed or other orthogonal matrices can be employed to equal effect. For example, the unipolar form applies in a similar manner. It should further be noted that the order of the matrix is not limited to two and can readily be extended to a higher order. In aspects, there are higher order corresponding orthogonal bases and matrices for computation. For example, a bipolar Hadamard matrix of size four by four is:

$$\begin{bmatrix} 1 & 1 & 1 & 1 \\ 1 & -1 & 1 & -1 \\ 1 & 1 & -1 & -1 \\ 1 & -1 & -1 & 1 \end{bmatrix} \qquad \text{Matrix 5}$$

Other orthogonal matrices and operators, including non-unitary matrices, matrices with non-zero traces, etc. can be employed to equal effect. The use of a Hadamard matrix is meant to be illustrative and not limiting.

In some examples, after the mixed signals 310 are transmitted 308, the mixed signals 310 are received 312 as Mode 1 signals 314, Mode 2 signals 316, Mode 3 signals 318, etc. In aspects, because the encoding mechanism is known, the reversed decoding process is used to unmix the mixed signals. In examples using Hadamard encoding, the decoding matrix is the same as the encoding Hadamard matrix.

Figure 4:
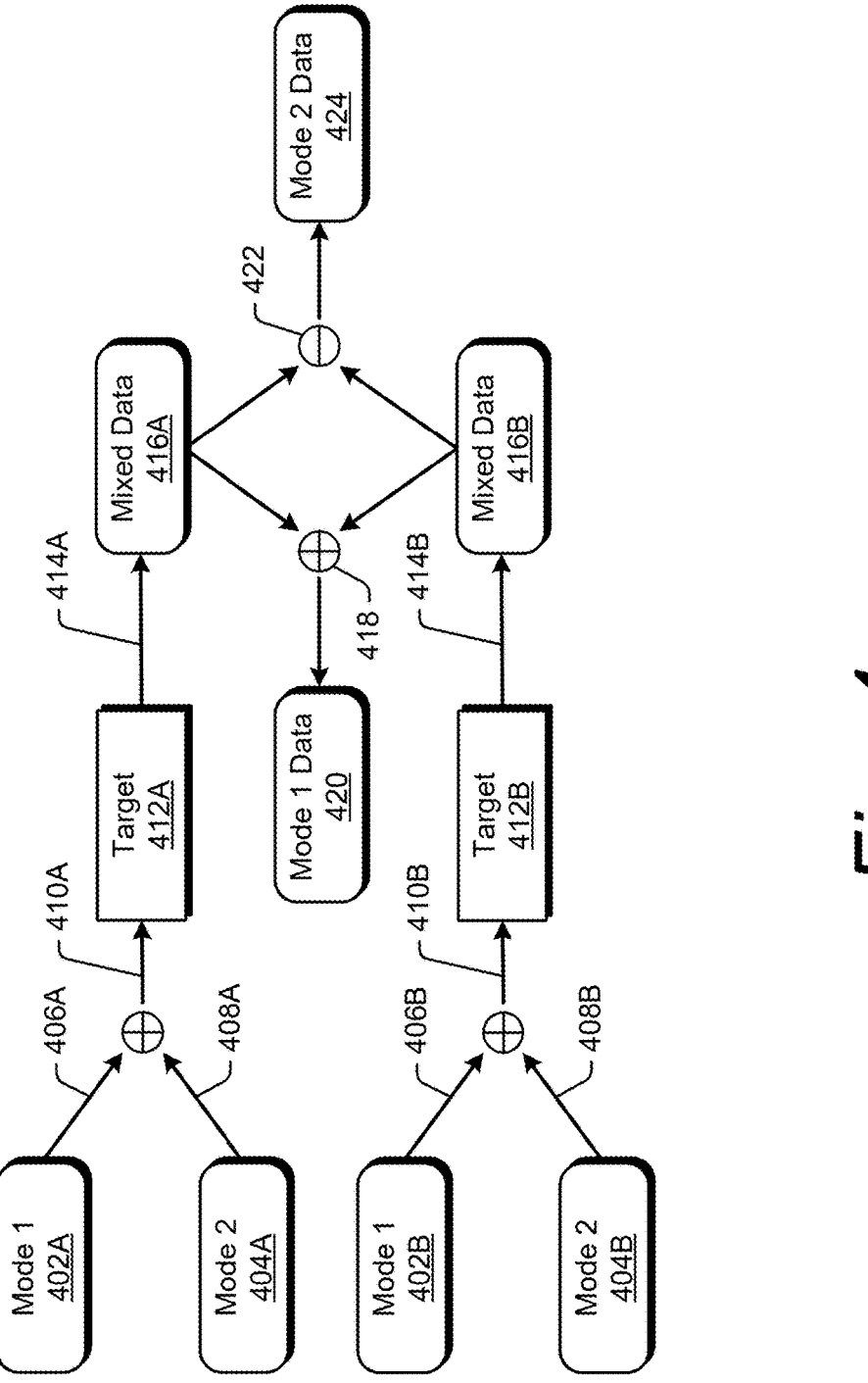
FIG. 4 illustrates a block diagram of an example encoding and decoding sequence for two mode types or two variants of the same mode type.

FIG. 4 illustrates a block diagram 400 of an example encoding and decoding sequence for two mode types or two variants of the same mode type. The block diagram 400 is an example of bipolar Hadamard encoding and decoding processes for two modes, Mode 1 402A, 402B and Mode 2 404A, 404B. In aspects, the transmission signals 406A and 406B represent Mode 1 based signals (402A and 402B, respectively), and the signals 408A and 408B represent Mode 2 based signals (404A and 404B, respectively). In aspects, transmission signals 406A and 408A are mixed, with both having positive polarity, as mixed signal 410A, and the mixed signal 410A is incident on a target 412A. The target 412A, according to some examples, returns a reception signal 414A, which can be recorded as mixed data 416A. In aspects, the mixed data 416A can be expressed as a combination of received radio frequency (RF) pings $RF_{406}$ and $RF_{408}$ as:

$$416A = RF_{406} + RF_{408} \qquad \text{Eq. 1}$$

In Eq. 1, $RF_{406}$ is the RF data corresponding with the Mode 1 402A from the transmission signal 406A and $RF_{408}$ is the RF data corresponding with the Mode 2 404A from the transmission signal 408A. Information for both $RF_{406}$ and $RF_{408}$ are contained in the mixed data 416A.

In aspects, transmission signals 406B and 408B are mixed with positive and negative polarity, respectively, as mixed signal 410B, and the mixed signal 410B is incident on a target 412B (which, in some examples, can be the same target as target 412A). In aspects, the mixed data 416B can be expressed as a combination of received RF pings $RF_{406}$ and $RF_{408}$ as:

$$416B = RF_{406} - RF_{408} \qquad \text{Eq. 2}$$

In Eq. 2, $RF_{406}$ is the RF data corresponding with the Mode 1 402B from the transmission signal 406B and $RF_{408}$ is the RF data corresponding with the Mode 2 404B from the transmission signal 408B. Note that RF ping $RF_{406}$ is the same for Mode 1 406A and Mode 1 406B and RF ping $RF_{408}$ is the same for Mode 2 408A and Mode 2 408B as these modes are the same mode type.

In aspects, the RF data of the Mode 1 (402A and 402B, which is $RF_{404}$), and the RF data of the Mode 2 (404A and 404B, which is $RF_{408}$) can be easily recovered based on Eqs. 1 and 2 as follows:

$$RF_{406} = (416A + 416B)/2 \qquad \text{Eq. 3}$$

$$RF_{408} = (416A - 416B)/2 \qquad \text{Eq. 4}$$

It should be readily apparent that the formulation of Eqs. 3 and 4 is equivalent to the bipolar Hadamard matrix of size 2 by 2, as in Matrix 1. This follows from the polarities used in mixing the mixed signal 410A and the mixed signal 410B.

In this way, the Hadamard matrix of size 2 by 2, in this example, can be used in both encoding and decoding using either two distinct mode types or two variants of the same mode type. In aspects, the additive operation Eq. 1 can be represented as a data addition 418, resulting in Mode 1 data 420, and the negative operation Eq. 2 can be represented as a data subtraction 422, resulting in Mode 2 data 424.

Figure 5:
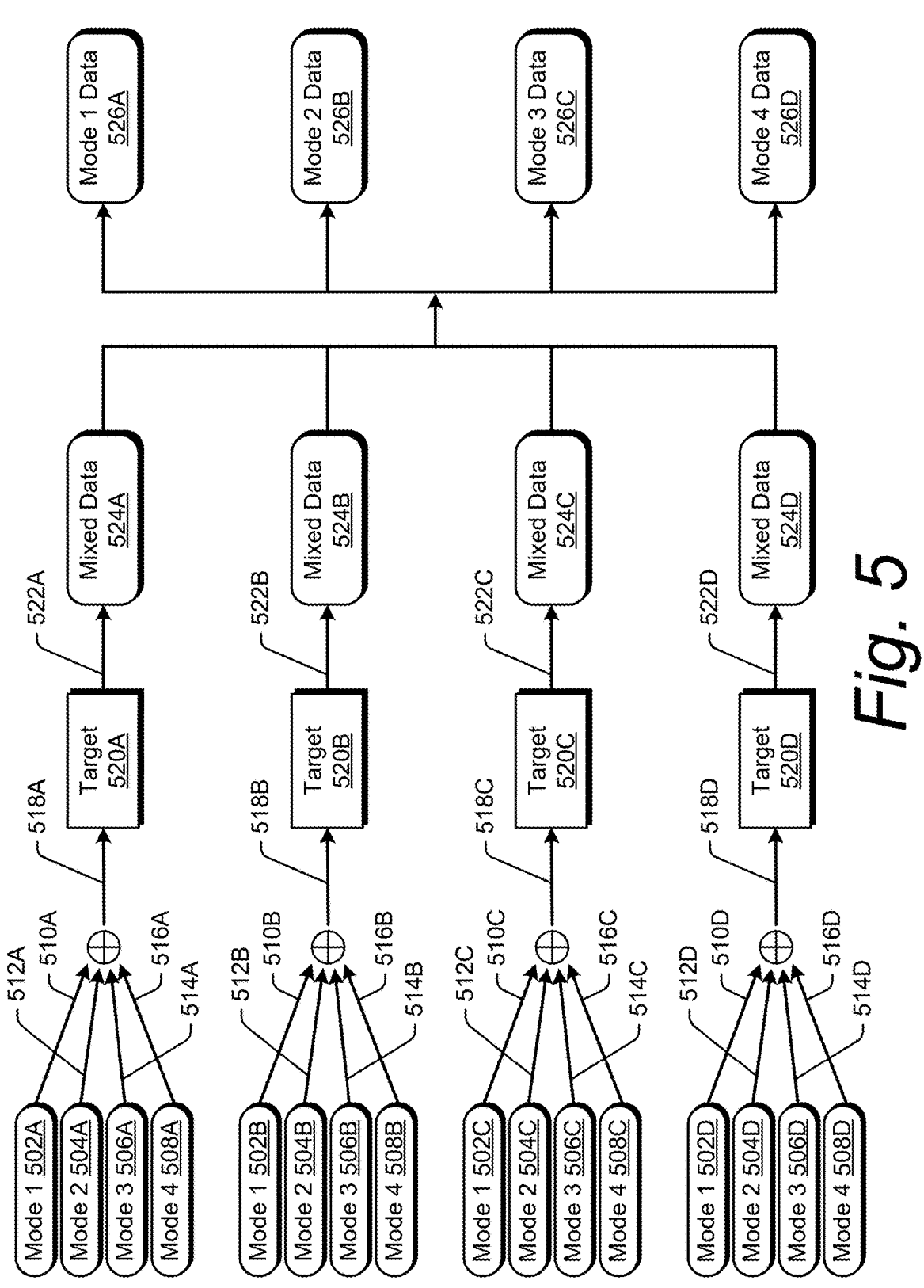
FIG. 5 illustrates a block diagram of an example encoding and decoding sequence for four mode types or variants of the same mode type.

FIG. 5 illustrates a block diagram 500 of an example encoding and decoding sequence for four mode types or variants of the same mode type. Throughout the following discussion, the technique will refer to "four modes," but it should be understood to include schemes where there is a mix between different mode types and variants within a single mode type, or simply four variants within a mode type in addition to four distinct mode types. To encode and decode four modes, in aspects, a fourth order Hadamard matrix can be used, such as the bipolar Hadamard matrix of Matrix 5. Mode 1 502A through Mode 4 508A can be, in aspects, related to respective transmission signals 510A-516A. In aspects, the transmission signals 510A-516A are mixed with positive polarities into a mixed signal 518A and directed at a target 520A. The target 520A, according to some examples, returns a reception signal 522A, which can be recorded as mixed data 524A. In aspects, the mixed data 524A can be expressed as a combination of received RF pings $RF_{510}$, $RF_{512}$, $RF_{514}$, and $RF_{516}$ as:

$$524A = RF_{510} + RF_{512} + RF_{514} + RF_{516} \qquad \text{Eq. 5}$$

In Eq. 5, $RF_{510}$ is the RF data corresponding with the Mode 1 502A from the transmission signal 510A and $RF_{512}$ is the RF data corresponding with the Mode 2 504A from the transmission signal 512A. In addition, $RF_{514}$ is the RF data corresponding with the Mode 3 506A from the transmission signal 514A and $RF_{516}$ is the RF data corresponding with the Mode 1 508A from the transmission signal 516A.

Similarly, in aspects, Mode 1 502B through Mode 4 508B are related to transmission signals 512B-516B combined as mixed signals 518B, which are aimed at a target 520B, resulting in reception signals 522B giving mixed data 524B. According to some examples, the transmission signals 510B-516B are mixed with polarities corresponding to row two of the bipolar Hadamard matrix of Matrix 5, allowing the mixed data 524B to be expressed as a combination of received RF pings $RF_{510}$, $RF_{512}$, $RF_{514}$, and $RF_{516}$ as:

$$524B = RF_{510} - RF_{512} + RF_{514} - RF_{516} \qquad \text{Eq. 6}$$

Similarly, in aspects, Mode 1 502C through Mode 4 508C are related to transmission signals 512C-516C combined as mixed signals 518C, aimed at a target 520C, resulting in reception signals 522C giving mixed data 524C. According to some examples, the transmission signals 510C-516C are mixed with polarities corresponding to row three of the bipolar Hadamard matrix of Matrix 5, allowing the mixed data 524C to be expressed as a combination of received RF pings $RF_{510}$, $RF_{512}$, $RF_{514}$, and $RF_{516}$ as:

$$524C = RF_{510} + RF_{512} - RF_{514} - RF_{516} \qquad \text{Eq. 7}$$

Similarly, in aspects, Mode 1502D through Mode 4 508D are related to transmission signals 512D-516D combined as mixed signals 518D, aimed at a target 520D, resulting in reception signals 522D giving mixed data 524D. According to some examples, the transmission signals 510D-516D are mixed with polarities corresponding to row four of the bipolar Hadamard matrix of Matrix 5, allowing the mixed data 524D to be expressed as a combination of received RF pings $RF_{510}$, $RF_{512}$, $RF_{514}$, and $RF_{516}$ as:

$$524D = RF_{510} - RF_{512} - RF_{514} + RF_{516} \qquad \text{Eq. 8}$$

As in the 2 by 2 case shown in FIG. 4, recovery of the RF data for Mode 1 (502A through 502D) through Mode 4 (508A through 508D) can be, in aspects, performed using Eqs. 5-8 as follows:

$$RF_{510} = 524A + 524B + 524C + 524D \qquad \text{Eq. 9}$$

$$RF_{512} = 524A - 524B + 524C - 524D \qquad \text{Eq. 10}$$

$$RF_{514} = 524A + 524B - 524C - 524D \qquad \text{Eq. 11}$$

$$RF_{516} = 524A - 524B - 524C + 524D \qquad \text{Eq. 12}$$

Though, in this example, the magnitude can be increased, this is immaterial to the data recapture as it only represents a scaling factor. It should be readily apparent that this formulation is equivalent to the bipolar Hadamard matrix of size four by four, as in Matrix 5. In this way, the Hadamard matrix of size four by four, in this example, can be used in both encoding and decoding using either distinct mode types, variants of the same Mode type, or a mix of both.

Figure 6:
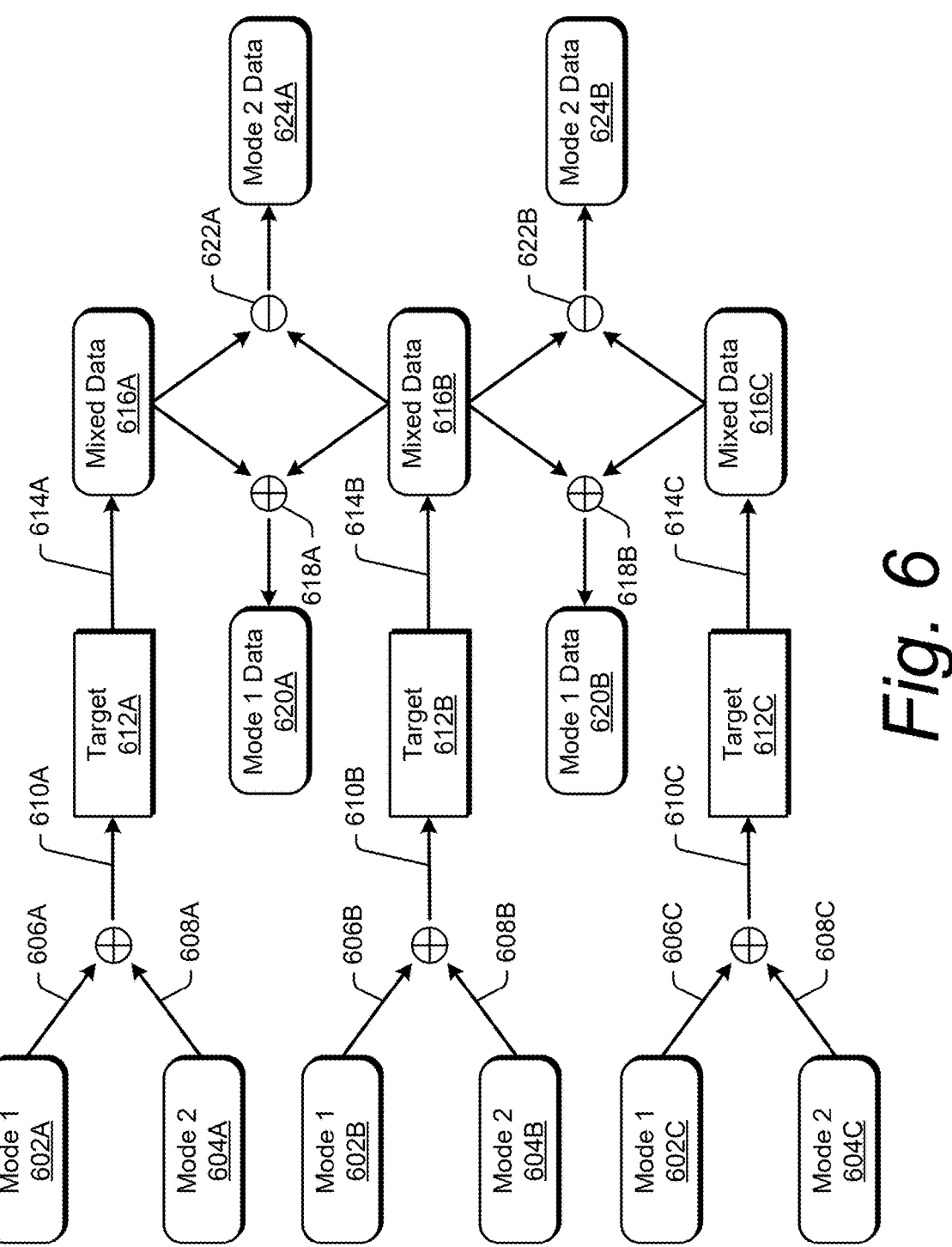
FIG. 6 illustrates a block diagram of an example encoding and decoding sequence.

FIG. 6 illustrates a block diagram 600 of an example encoding and decoding sequence. In aspects, the example of FIG. 4 does not enable an increase over standard ultrasound frame rates as there are still only two data recovered (420 and 424) from the initial two transmissions (410A and 410B). To increase frame rate, some examples can include a third transmission signal (or more transmission signals, e.g., four, five, etc.). Considering FIG. 6, in aspects, Modes 1 and 2 (602A through 602C and 604A through 604C, respectively) are related to transmission signals 606A through 606C and 608A through 608C, respectively, and combined into mixed signals 610A through 610C, respectively. The mixed signals 610A through 610C are aimed at targets 612A through 612C, respectively, resulting in reception signals 614A through 614C, respectively, and giving mixed data 616A through 616C, respectively.

In aspects, the transmission signals 610A through 610C can be mixed with different polarities in order to recover received RF pings corresponding to the Modes 1 (602A through 602C) and 2 (604A through 604C) via the transmission signals 606A through 606C and 608A through 608C, respectively, represented as received RF pings $RF_{606}$ and $RF_{608}$, respectively. In this way, the received mixed data 616A through 616C can contain information on the RF pings as follows:

$$616A = RF_{606} + RF_{608} \qquad \text{Eq. 13}$$

$$616B = RF_{606} - RF_{608} \qquad \text{Eq. 14}$$

$$616C = RF_{606} + RF_{608} \qquad \text{Eq. 15}$$

According to some examples, the encoding scheme resulting in Eqs. 13-15 can be used to recover Mode 1 data 620A and 620B using addition operators 618A and 618B and Mode 2 data 624A and 624B using subtraction operators 622A and 622B as follows:

$$620A = 616A + 616B \qquad \text{Eq. 17}$$

$$620B = 616B + 616C \qquad \text{Eq. 18}$$

$$624A = 616A - 616B \qquad \text{Eq. 19}$$

$$624B = 616B - 616C \qquad \text{Eq. 20}$$

Combining Eqs. 13-15 with Eqs. 16-19 results in the following:

$$620A = RF_{606} + RF_{608} + RF_{606} - RF_{608} \qquad \text{Eq. 20}$$

$$620B = RF_{606} - RF_{608} + RF_{606} + RF_{608} \qquad \text{Eq. 21}$$

$$624A = RF_{606} + RF_{608} - RF_{606} + RF_{608} \qquad \text{Eq. 22}$$

$$624B = RF_{606} - RF_{608} - RF_{606} - RF_{608} \qquad \text{Eq. 23}$$

$$RF_{606} = \frac{620A}{2} = \frac{620B}{2} \qquad \text{Eq. 24}$$

$$RF_{608} = \frac{624A}{2} = -\frac{624B}{2} \qquad \text{Eq. 25}$$

In aspects, the example of FIG. 6 has three outgoing signals in mixed signals 610A, 610B, and 610C, but four received data signals in Mode 1 data 620A and 620B and Mode 2 data 624A and 624B, resulting in a frame rate increase of 4/3. This gives the following formula for the number of frames M given the outlined rolling encoding/ decoding scheme with N input pings:

$$M = 2N - 2 \qquad \text{Eq. 26}$$

Thus, in aspects, the rolling encoding scheme of FIG. 6 effectively doubles the frame rate, less the first and last pings. In this example, every additional ping over the first ping (and aside from the last ping) generates two additional data. Although two mode types were outlined, this should not be seen as limiting. Similar frame rate gains can be realized using higher order mode type counts, such as three, four, etc.

In aspects, a potential issue in actual applications is that ping positions cannot be constant, for example in B-mode. In examples of this kind, the correlation among different pings cannot be maintained, causing issues in implementing some or all of the aforementioned encoding/decoding processes. To address this issue, some example embodiments of a multi-mode rolling-encoded ultrasound can include a spatial rolling-encoding and decoding process, as shown in FIG. 7.

Figure 7:
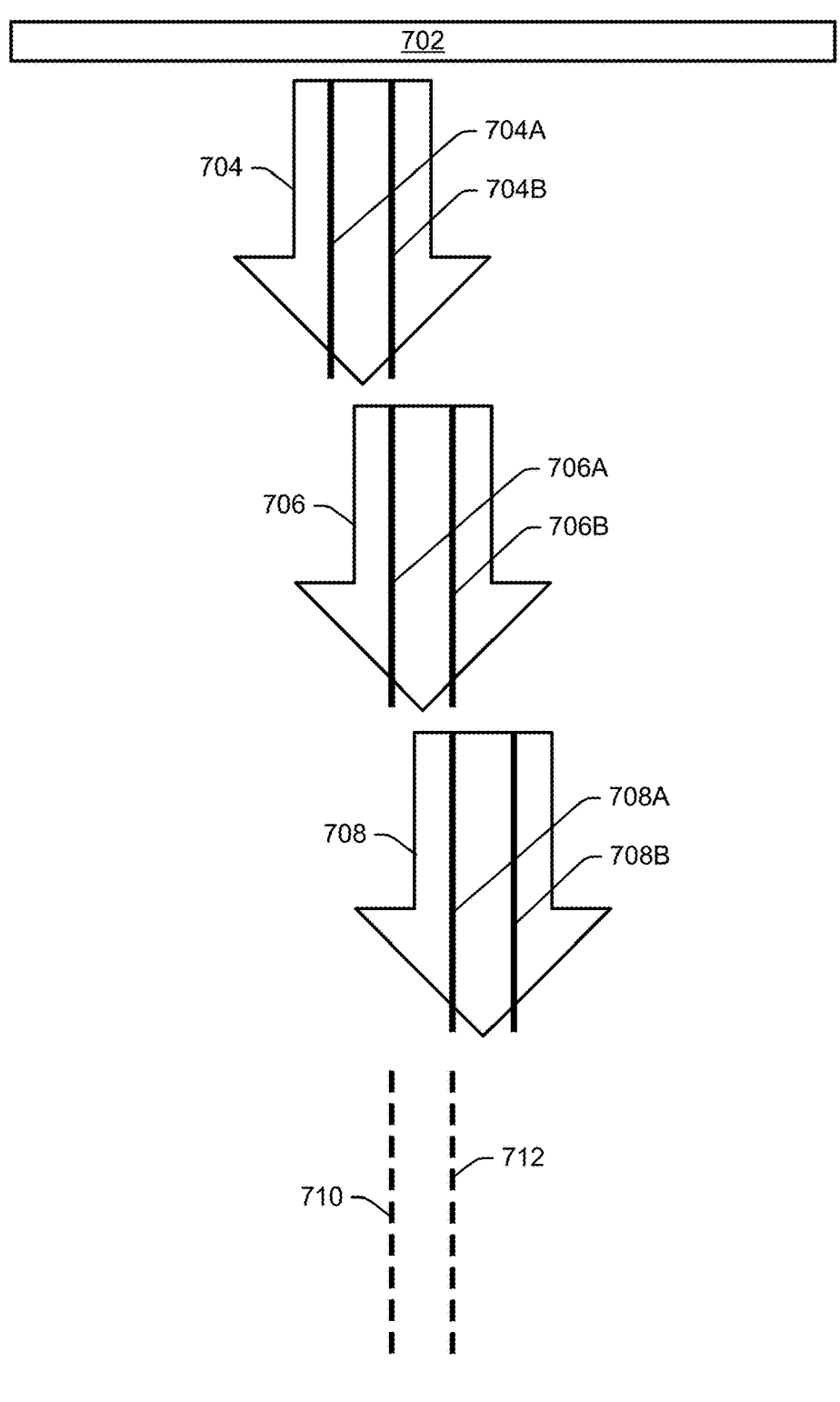
FIG. 7 illustrates an example of a rolling encoding mechanism in space.

FIG. 7 illustrates an example of a rolling-encoding mechanism 700 in space. In this embodiment, a transducer 702 (e.g., the scanner 104) can take advantage of a broader transmission and multi-line (ML) reception. For each of these two or more transmissions, in aspects, there can be two or more corresponding receptions and RF data. In some examples, there can be a series of pings sent out with multi-mode encoding. In FIG. 7, dual mode type or mode variant pings are used, though more mode types or variants within a mode type can equivalently be used. For example, a multi-mode ping 704 can be sent with a Mode 704A and a Mode 704B. In aspects, a multi-mode ping 706 can be sent with a Mode 706A and a Mode 706B, and a multi-mode ping 708 can be sent with a Mode 708A and a Mode 708B. Note that Modes 704B and 706A overlap in space at line 710 and Modes 706B and 708A overlap in space at line 712.

Spatial rolling-encoding can be realized in a similar fashion as the multi-mode encoding of previous examples, such as that shown in FIGS. 4, 5, and 6. Again using the non-limiting example of a bipolar Hadamard matrix encoding and decoding, Modes 704A, 706A, 708A, 704B, 706B, and 708B can use multi-mode types. The first mode type can, in some examples, correspond with received RF pings represented by $RF_1$ and the second mode type can correspond with received RF pings represented by $RF_2$. The encoding in such an example, when using a bipolar Hadamard matrix encoding, has the following representation:

$$704B = RF_1 + RF_2 \qquad \text{Eq. 27}$$

$$706A = RF_1 - RF_2 \qquad \text{Eq. 28}$$

$$706B = RF_1 - RF_2 \qquad \text{Eq. 29}$$

$$708A = RF_1 + RF_2 \qquad \text{Eq. 30}$$

Reception of these Modes $RF_1$ and $RF_2$ can be recovered from signals received as a multi-mode reception signal, such as those originating at the lines 710 and 712. In aspects, as the line 710 represents a region of space where the Modes 704B and 706A are incident and the line 712 represents a region of space where the Modes 706B and 708A are incident. For example, taking the polarities of Eqs. 27-30, results in the following equations:

$$RF_1 = (704B + 706A)/2 \qquad \text{Eq. 31}$$

$$RF_2 = (704B - 706A)/2 \qquad \text{Eq. 32}$$

$$RF_1 = (706B + 708A)/2 \qquad \text{Eq. 33}$$

$$RF_2 = (708A - 706B)/2 \qquad \text{Eq. 34}$$

According to the illustrated example of FIG. 7, Eqs. 31 and 32 are using data from signals originating at the line 710 and Eqs. 33 and 34 are using data from signals originating at the line 712. Thus, in examples and embodiments with spatial rolling encoding and decoding as outlined, the issue of pings originating from variable points in space can be resolved.

In addition to resolving, in aspects, the spatial encoding problem, the example of spatial rolling encoding and decoding shown by FIG. 7 also can be used to increase the frame rate. If, for example, N is the level of encoding, each ping 704, 706, and 708 has two corresponding multi-mode signals with N=2. As detailed by Eqs. 31-34, data recovery here is four frames of data (two of $RF_1$ and two of $RF_2$). Each multi-mode signal 706A and 706B corresponds with two received data frames, giving the ping 706 four recovered data frames with only two sent signals (the multi-modes 706A and 706B). In aspects, the frame rate for such a multi-mode rolling spatial encoding and decoding scheme with multi-modes of order N and outgoing signals of order M gives a frame rate F of:

$$F = M * N \qquad \text{Eq. 35}$$

Though the discussion of the multi-mode rolling spatial encoding and decoding scheme of FIG. 7 uses the example of two multi-modes per ping, with each multi-mode consisting of two mode types and using a Hadamard bipolar matrix operation for polarity and recombination, this should not be seen as limiting. Other orders for the pings and mode types can be used, as well as different encoding and decoding operators.

Figure 8:
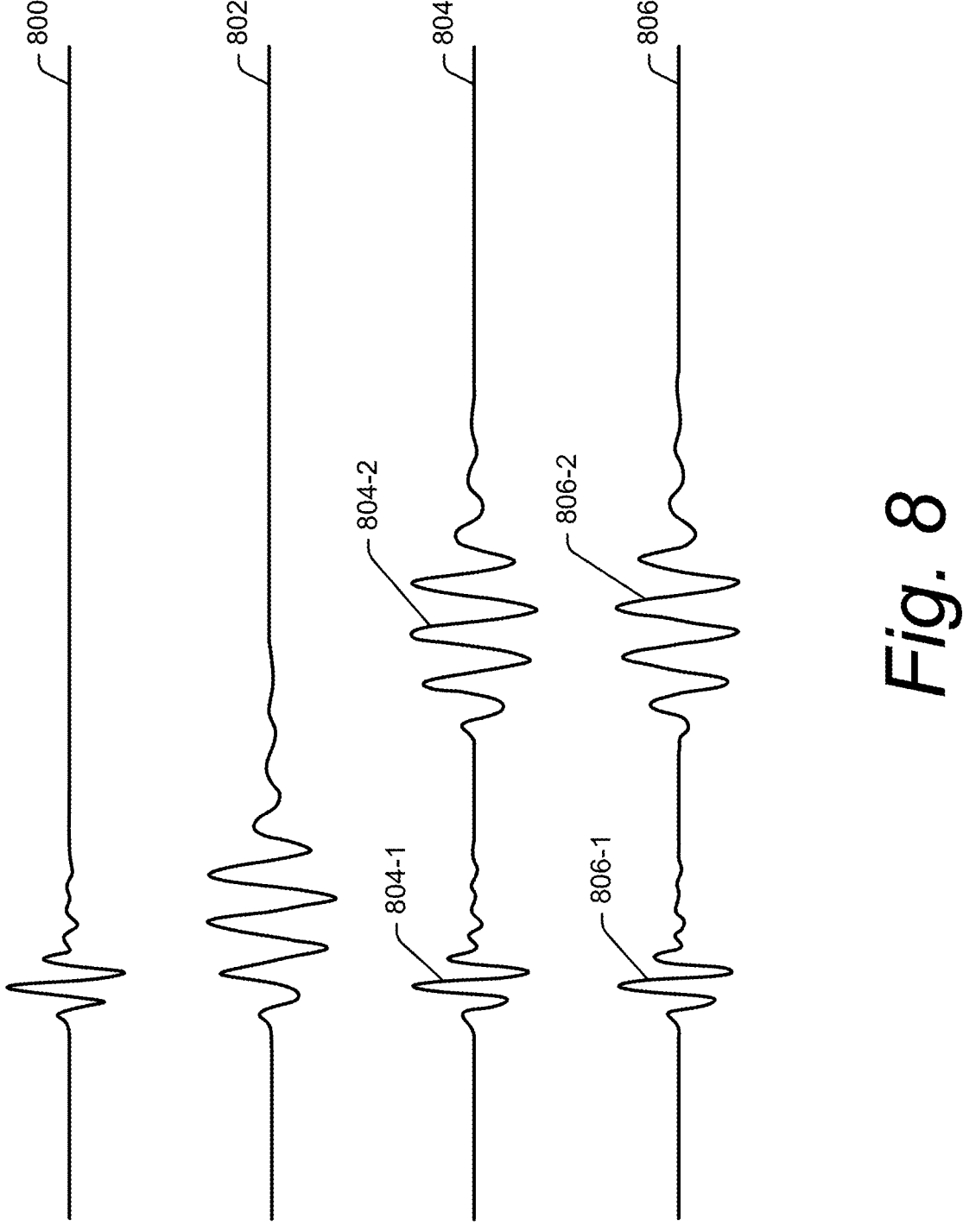
FIG. 8 illustrates example waveforms for a multi-mode rolling-encoded ultrasound.

FIG. 8 illustrates example waveforms for a multi-mode rolling-encoded ultrasound. Waveform 800 is an example of a B-mode waveform. Waveform 802 is an example of a PW waveform. In aspects, the waveforms 802 and 804 represent two different mode types. Other mode types can be used equally, as discussed, but for this example only a B-mode and a PW waveform are used to aid in illustration.

In a typical ultrasound transducer, the B-mode waveform 800 and the PW waveform 802 can, in aspects, be sent as separate wave pulses or pings. In some examples, a multi-mode rolling-encoded ultrasound can combine the waveforms 800 and 802 into a single ping. Waveform 804 is an example of a B-mode 804-1 and a PW waveform 804-2 in the same ping. Here, the encoding for the waveform 804 uses a positive polarity B-mode 804-1 and a positive polarity PW waveform 804-2, as in the waveforms 800 and 802.

In order to encode with negative signs, as in the examples discussed earlier using bipolar Hadamard matrix encoding and decoding, the polarity of one or more of the mode types encoded into an encoded waveform can be switched. An example of this is waveform 806. The waveform 806, in aspects, contains a B-mode 806-1 (as in the waveform 800) and a PW 806-2 (as in the waveform 802) waveform, but the PW portion 806-2 has had its polarity flipped. Comparing the PW portion 806-2 of the waveform 806 and the PW portion 804-2 of the waveform 804 illustrates this example polarity reversal. The flipping or reversal of a polarity can, in aspects, correspond with a negative sign in an encoding or decoding operator, such as the negative signs found in a bipolar Hadamard matrix operator.

Figure 9:
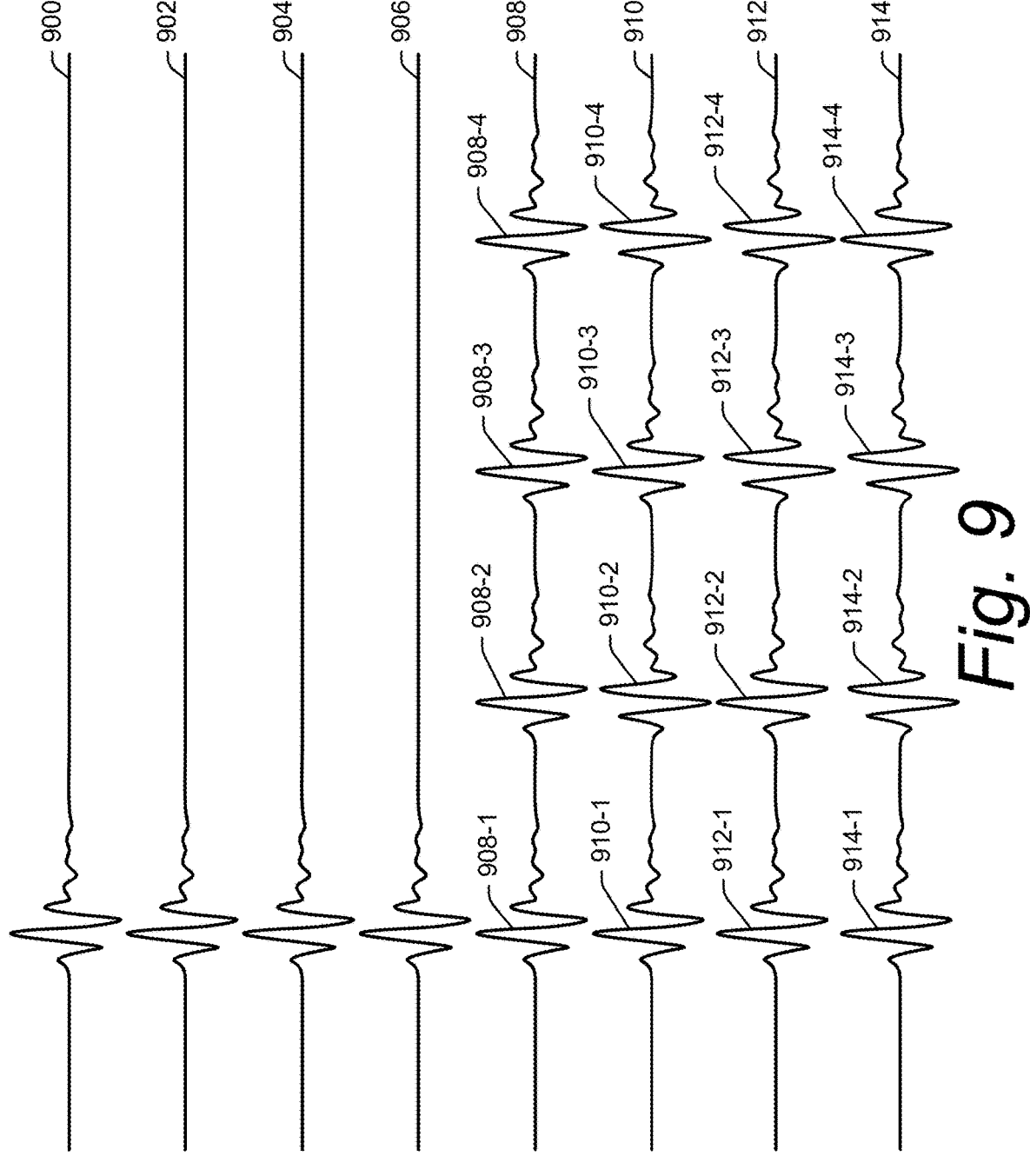
FIG. 9 illustrates additional example waveforms for a multi-mode rolling-encoded ultrasound.

FIG. 9 illustrates additional example waveforms for a multi-mode rolling-encoded ultrasound. Instead of using different mode types, waveforms 900-914 represent the same mode type with different variants. In aspects, the waveforms 900-914 can be B-mode waveforms with four distinct angles. The waveforms 900-906 represent single B-mode waveforms, while the waveforms 908-914 represent multi-mode B-mode waveforms. Each of the multi-mode waveforms 908-914, in aspects, has an encoding for the B-mode varieties included.

For example, the single-mode waveforms 900-906 can be positive polarity waveforms. Note each of the waveforms 900-906 have the same shape as they are all B-mode waveforms in this example. The multi-mode waveform 908 includes all of the B-mode waveforms 908-1, 908-2, 908-3, and 908-4 from the waveforms 900, 902, 904, and 906 in positive polarity. This is, in aspects, a representation of the first row of a four by four Hadamard matrix, such as the Hadamard matrix of Matrix 5. This can, in aspects, be represented as a vector, (1, 1, 1, 1).

In another example, the multi-mode waveform 910 includes all of the waveforms 910-1, 910-2, 910-3, and 910-4 from the single-mode waveforms 900, 902, 904, and 906, but the polarities are not all positive. The waveform portions 910-2 and 910-4 both have negative polarities, while the waveform portions 910-1 and 910-3 both have positive polarities. In this example, the waveform 910 follows the second row of the Hadamard matrix of Matrix 5. This can, in aspects, be written as a vector, (1, −1, 1, −1).

In another example, the multi-mode waveform 912 includes all of the waveforms 912-1, 912-2, 912-3, and 912-4 from the single-mode waveforms 900, 902, 904, and 906, but the polarities are not all positive. The waveform portions 912-3 and 912-4 both have negative polarities, while the waveform portions 912-1 and 912-2 both have positive polarities. In this example, the waveform 912 follows the third row of the Hadamard matrix of Matrix 5. This can, in aspects, be written as a vector, (1, 1, −1, −1).

In another example, the multi-mode waveform 914 includes all of the waveforms 914-1, 914-2, 914-3, and 914-4 from the single-mode waveforms 900, 902, 904, and

906, but the polarities are not all positive. The waveform portions 914-2 and 914-3 both have negative polarities, while the waveform portions 914-1 and 914-4 both have positive polarities. In this example, the waveform 914 follows the fourth row of the Hadamard matrix of Matrix 5. This can, in aspects, be written as a vector, (1, −1, −1, 1).

In this embodiment, the multi-mode waveforms, via the polarities of their constituent components, represent the Hadamard matrix of Matrix 4, namely:

$$\begin{bmatrix} 1 & 1 & 1 & 1 \\ 1 & -1 & 1 & -1 \\ 1 & 1 & -1 & -1 \\ 1 & -1 & -1 & 1 \end{bmatrix} \qquad \text{Matrix 6}$$

In the Hadamard matrix example of Matrix 6, each row 1-4 corresponds to the multi-mode waveforms 908-914, respectively, and each column 1-4 corresponds to the single-mode waveforms 900-906, respectively. In this way, encoding and decoding of multi-mode waveforms can be performed as previously outlined. It should be understood that, although this example uses multiple-angle B-mode mode type variants, four by four bipolar Hadamard encoding, and linear encoding (e.g., the multi-mode waveforms 908-914 have one waveform component after another in the encoding and propagation scheme), the techniques disclosed herein are not limited to these examples. Alternate mode type variants can also be used, different encoding and decoding methods (e.g., Fourier matrix, non-orthogonal matrix, etc.) can be implemented, and non-linear waveform combination techniques (e.g., stacked waves, superposition, etc.) can be applied.

Example Method

FIG. 10 outlines a method 1000 for a multi-mode rolling-encoded ultrasound. The method 1000 can be performed by an ultrasound machine, such as the ultrasound machine 200 described herein. At 1002, a first ultrasound signal is encoded as a mixed waveform. In aspects, the first ultrasound signal includes a plurality of ultrasound signal modes and is configured for transmission at a subject. According to some examples, the ultrasound signal modes include two or more of an A-mode, a B-mode, an M-mode a Doppler-based mode, a non-image based mode, and/or different variants of these modes. Encoding of the mixed waveform can, in aspects, follow the disclosed methodology used to encode the waveforms 908-914. The encoding can be accomplished, in some examples, using a bipolar Hadamard matrix, a Fourier matrix, another orthogonal operator, a non-orthogonal encoding operation, etc. In aspects, the mixed waveform can be encoded with linear waveform components, such that each component of the multi-mode signal follows the previous component. Additionally or alternately, the mixed waveform can be encoded in a non-linear fashion, for example using a superposition of constituent waveform components. Other encoding techniques known to a person of ordinary skill in the art can also be employed. In some examples, the encoding of the ultrasound signal includes combining the plurality of ultrasound signal modes based on at least one of a polarity, a time of transmission, or a location of transmission.

At 1004, the first ultrasound signal is generated. The signal generation can be, in some examples, performed with an ultrasound transducer, such as the transducer assembly 214. In examples where the generation of the first ultrasound signal is intended to be part of an ultrasound examination or scan, the first ultrasound signal can be incident upon an anatomy of a patient or some other structure. In aspects, the first ultrasound signal can propagate in a medium and reflect off the anatomy or the structure being imaged.

At 1006, an encoded second ultrasound signal is received. In aspects, the received encoded second ultrasound signal can be based on the first encoded ultrasound signal sent to and reflected from the anatomy or the structure being imaged. Receipt of the encoded second ultrasound signal can be performed by the ultrasound transducer, such as the ultrasound transducer assembly 214.

At 1008, the received encoded second ultrasound signal is decoded into ultrasound data. In examples where the encoding of step 1002 was performed using a bipolar Hadamard matrix, the same bipolar Hadamard matrix can be used for the decoding 1008. By way of example, the bipolar Hadamard matrix of Matrix 5 can be used. This is meant to be illustrative and not limiting, as there are many other encoding and decoding schemes, which can be employed with similar effect (e.g., unipolar Hadamard matrix operators, Fourier matrix operators, other orthogonal matrix operators, non-orthogonal operators, etc.).

At 1010, an output is generated based on the ultrasound data. The output can be an image, such as an image of the anatomy or the structure being imaged. In other examples, the output can be a message to a user, such as a status message, an indication of the presence of a disease or a condition, an indication of a parameter (e.g., a speed of sound in the medium, a background noise level, etc.), or any other message that relays information related to the ultrasound data. In aspects, the mixed waveform can contain single-mode waveforms configured to relay or otherwise generate non-image data related to the anatomy, the structure, the medium, or any other aspect of the ultrasound examination or scan.

Optionally, at 1012, a filtered ultrasound data is generated. In aspects, the filtered ultrasound data is generated based on the ultrasound data. At 1014, an output is generated based on the filtered ultrasound data. In aspects, the output generated at 1014 can be materially similar to the output generated at 1010, but the output of 1014 is based on the filtered ultrasound signal and not the ultrasound signal.

Conclusion

Embodiments of a multi-mode rolling-encoded ultrasound as described herein are advantageous, as they provide for both an increased resolution and increased frame rate in ultrasound scans, as well as a minimization of artifacts. The techniques of the multi-mode rolling-encoded ultrasound disclosed herein also avoid decorrelation issues often found in spatial ultrasound transducing methods, such as when a transducer generates pings in different areas in space during an ultrasound imaging. Further, the techniques described herein enable non-image outputs to be generated from the multi-mode rolling-encoded ultrasound, such as a determination of a speed of sound in a material, a background noise, or other useful parameters or information, which may not be available in an image output. The multi-mode rolling-encoded ultrasound provide increased scanning efficiency, improved patient experience, higher fidelity scanning outcomes, and similar benefits.

What is claimed is:

1. An ultrasound device comprising:
an ultrasound scanner configured to generate an ultrasound signal, the ultrasound signal:
    comprising a plurality of ultrasound signal modes; and
    configured for transmission by the ultrasound scanner at a subject;

one or more processors; and
a memory, the memory storing instructions that, when executed by the one or more processors, cause the one or more processors to encode the ultrasound signal as a mixed waveform based on the plurality of ultrasound signal modes, the mixed waveform comprising a superposition of the plurality of ultrasound signal modes.

2. The ultrasound device of claim 1, wherein the plurality of signal modes include two or more of an amplitude mode ("A-mode"), a brightness mode ("B-mode"), a motion mode ("M-mode"), a Doppler-based mode, and different variants of these modes.

3. The ultrasound device of claim 1, wherein at least one of the plurality of ultrasound signal modes is a non-image-based signal mode.

4. The ultrasound device of claim 1, wherein the mixed waveform comprises an addition of two or more of the plurality of ultrasound signal modes.

5. The ultrasound device of claim 1, wherein the ultrasound scanner is configured to transmit the encoded ultrasound signal at the subject.

6. The ultrasound device of claim 5, wherein the transmission of the encoded ultrasound signal is a single ping.

7. The ultrasound device of claim 1, wherein the encoding of the ultrasound signal comprises combining the plurality of ultrasound signal modes based on at least one of a polarity, a time of transmission, or a location of transmission.

8. The ultrasound device of claim 7, wherein the plurality of ultrasound signal modes are combined using an orthogonal matrix operator.

9. An ultrasound device comprising:
an ultrasound scanner, the ultrasound scanner configured to receive an encoded ultrasound signal, the encoded ultrasound signal comprising:
    reflections of a plurality of ultrasound signal modes from a subject;
one or more processors; and
a mixed waveform, the mixed waveform comprising a superposition of the plurality of ultrasound signal modes; and
a memory storing instructions that, when executed by the one or more processors, cause the one or more processors to decode the received encoded ultrasound signal into ultrasound data comprising the plurality of ultrasound signal modes.

10. The ultrasound device of claim 9, wherein plurality of ultrasound signal modes include two or more of an amplitude mode ("A-mode"), a brightness mode ("B-mode"), a motion mode ("M-mode"), a Doppler-based mode, and different variants of these modes.

11. The ultrasound device of claim 9, wherein the decoding of the received encoded ultrasound signal into the ultrasound data is based on one or more of a polarity, a time of transmission, or a location of transmission for the encoded ultrasound signal.

12. The ultrasound device of claim 9, wherein the instructions further cause the one or more processors to generate filtered ultrasound data based on the ultrasound data.

13. The ultrasound device of claim 9, wherein the decoding of the received encoded ultrasound signal into the ultrasound data comprises processing the received encoded ultrasound signal using an orthogonal matrix operator.

14. The ultrasound device of claim 9, wherein the instructions further cause the one or more processors to produce an output based on the ultrasound data.

15. The ultrasound device of claim 14, wherein the output is one or more of an image of an anatomy of the subject, a determination of a speed of sound, a determination of a background noise, and a detection of one or more artifacts.

16. An ultrasound device comprising:

an ultrasound scanner, the ultrasound scanner configured to:

generate a first ultrasound signal, the first ultrasound signal:

comprising a plurality of ultrasound signal modes; and configured for transmission by the ultrasound scanner at a subject; and receive an encoded ultrasound signal, the encoded ultrasound signal comprising reflections of the plurality of ultrasound signal modes from the subject;

one or more processors; and a memory, the memory storing instructions that, when executed by the one or more processors, cause the one or more processors to:

encode the first ultrasound signal as a mixed waveform based on the plurality of ultrasound signal modes, the mixed waveform comprising a superposition of the plurality of ultrasound signal modes; and decode the received encoded ultrasound signal into ultrasound data comprising the plurality of ultrasound signal modes.

17. The ultrasound device of claim 16, wherein the plurality of ultrasound signal modes are two or more of an amplitude mode ("A-mode"), a brightness mode ("B-mode"), a motion mode ("M-mode"), a Doppler-based mode, and different variants of these modes.

18. The ultrasound device of claim 16, wherein the encoding of the first ultrasound signal and the decoding of the received encoded ultrasound signal comprise processing the plurality of ultrasound signal modes and the received encoded ultrasound signal, respectively, using an orthogonal matrix operator.

19. The ultrasound device of claim 16, wherein the instructions further cause the one or more processors to:

produce, based on the ultrasound signal, filtered ultrasound data; and produce, based on the filtered ultrasound data, an output.

20. The ultrasound device of claim 19, wherein the output is one or more of an image of an anatomy of the subject, a determination of a speed of sound, a determination of a background noise, and a detection of one or more artifacts.

* * * * *